(12) United States Patent
Kiefer et al.

(10) Patent No.: US 8,945,827 B2
(45) Date of Patent: Feb. 3, 2015

(54) SEROLOGICAL METHODS AND DIAGNOSTIC TESTS FOR SYPHILIS ANTIBODIES

(71) Applicant: Awareness Technology Inc., Palm City, FL (US)

(72) Inventors: David J. Kiefer, Miami Springs, FL (US); Oscar R. Compain, Coral Gables, FL (US)

(73) Assignee: Awareness Technology, Inc., Palm City, FL (US)

( * ) Notice: Subject to any disclaimer, the term of this patent is extended or adjusted under 35 U.S.C. 154(b) by 0 days.

(21) Appl. No.: 14/191,014

(22) Filed: Feb. 26, 2014

(65) Prior Publication Data

US 2014/0273027 A1 Sep. 18, 2014

Related U.S. Application Data

(60) Provisional application No. 61/778,544, filed on Mar. 13, 2013.

(51) Int. Cl.

| | | |
|---|---|---|
| *C12Q 1/00* | (2006.01) | |
| *G01N 1/30* | (2006.01) | |
| *G01N 33/53* | (2006.01) | |
| *G01N 33/554* | (2006.01) | |
| *G01N 33/571* | (2006.01) | |
| *G01N 33/531* | (2006.01) | |

(52) U.S. Cl.
CPC ............ *G01N 33/571* (2013.01); *G01N 33/531* (2013.01)
USPC ............... 435/4; 435/7.1; 435/7.32; 435/40.5

(58) Field of Classification Search
None
See application file for complete search history.

(56) References Cited

U.S. PATENT DOCUMENTS

| | | | |
|---|---|---|---|
| 4,738,932 A * | 4/1988 | Yabusaki | 435/7.36 |
| 4,962,046 A | 10/1990 | Kapmeyer | |
| 5,231,035 A | 7/1993 | Akers, Jr. | |
| 5,279,935 A | 1/1994 | Nycz | |
| 5,561,070 A | 10/1996 | Stewart et al. | |
| 5,565,366 A | 10/1996 | Akers, Jr. | |
| 5,639,620 A | 6/1997 | Siiman et al. | |
| 5,776,706 A | 7/1998 | Siiman et al. | |
| 5,827,749 A | 10/1998 | Akers, Jr. | |
| 5,840,587 A | 11/1998 | Stewart et al. | |
| 6,423,270 B1 | 7/2002 | Wall | |
| 6,815,173 B1 | 11/2004 | Pope et al. | |
| 6,822,000 B2 | 11/2004 | Ng et al. | |
| 6,921,496 B2 | 7/2005 | Anderson et al. | |
| 6,946,145 B2 | 9/2005 | Ng et al. | |
| 7,005,270 B2 | 2/2006 | Liu et al. | |
| 7,335,736 B2 | 2/2008 | Liu et al. | |
| 7,470,379 B2 | 12/2008 | Anderson et al. | |
| 7,566,476 B2 | 7/2009 | Bawendi et al. | |
| 7,888,043 B2 | 2/2011 | Castro et al. | |
| 8,034,259 B2 | 10/2011 | Anderson et al. | |
| 8,071,359 B2 | 12/2011 | Weiss et al. | |
| 8,071,360 B2 | 12/2011 | Weiss et al. | |
| 8,071,361 B2 | 12/2011 | Weiss et al. | |
| 8,101,234 B2 | 1/2012 | Bawendi et al. | |
| 8,158,193 B2 | 4/2012 | Bawendi et al. | |
| 8,192,646 B2 | 6/2012 | Anderson et al. | |
| 8,288,152 B2 | 10/2012 | Weiss et al. | |
| 8,288,153 B2 | 10/2012 | Weiss et al. | |
| RE43,914 E | 1/2013 | Castro | |
| 8,481,112 B2 | 7/2013 | Bawendi et al. | |
| 8,481,113 B2 | 7/2013 | Bawendi et al. | |
| 8,639,449 B2 | 1/2014 | Weiss et al. | |
| 8,778,619 B2 | 7/2014 | Castro et al. | |

\* cited by examiner

*Primary Examiner* — Albert Navarro
(74) *Attorney, Agent, or Firm* — Mayback & Hoffman P.A.; Gregory L. Mayback

(57) ABSTRACT

A non-treponemal diagnostic test for syphilis infection includes initially dissolving cholesterol in an organic solvent and further diluting the dissolved cholesterol in an ethanol solution comprising cardiolipin and lecithin, permitting a volume of the antigen solution to evaporate in place within a container, rinsing the coated container with buffered saline, stabilizing the antigen coating by overcoating the antigen coating with an inert protein dissolved in buffered saline, decanting the overcoat solution, air-drying the container, and sealing the container in vapor-proof pouches with desiccant, providing an enzyme-labeled conjugate component of a syphilis infection test that is formulated to be compatible with a lipid nature of the cholesterol, the cardiolipin, and the lecithin VDRL antigens, providing a sample diluent that is formulated to be compatible with the lipid nature of the VDRL antigens, and providing a wash fluid that is formulated to be compatible with the lipid nature of the VDRL antigens.

21 Claims, 5 Drawing Sheets

SEROLOGICAL METHODS AND DIAGNOSTIC TESTS FOR SYPHILIS ANTIBODIES

CROSS-REFERENCE TO RELATED APPLICATION

This application claims the priority, under 35 U.S.C. §119, of U.S. Provisional Patent Application No. 61/778,544, filed Mar. 13, 2013; the prior application is herewith incorporated by reference herein in its entirety.

STATEMENT REGARDING FEDERALLY SPONSORED RESEARCH OR DEVELOPMENT

Not Applicable

FIELD OF THE INVENTION

The present invention lies in the field of medical testing. The present disclosure relates to serological methods and diagnostic tests for syphilis antibodies.

BACKGROUND OF THE INVENTION

Syphilis is a sexually transmitted infection caused by the spirochete bacterium *treponema pallidum* subspecies *pallidum*. The primary route of transmission is through sexual contact; it may also be transmitted from mother to fetus during pregnancy or at birth, resulting in congenital syphilis. Other human diseases caused by related *treponema pallidum* include yaws (subspecies *pertenue*), pinta (subspecies *carateum*), and bejel (subspecies *endemicum*).

The signs and symptoms of syphilis vary depending in which of the four stages it presents (primary, secondary, latent, and tertiary). The primary stage classically presents with a single chancre (a firm, painless, non-itchy skin ulceration), secondary syphilis with a diffuse rash which frequently involves the palms of the hands and soles of the feet, latent syphilis with little to no symptoms, and tertiary syphilis with gummas, neurological, or cardiac symptoms. It has, however, been known as "the great imitator" due to its frequent atypical presentations. Diagnosis is usually via blood tests; however, the bacteria can also be detected using dark field microscopy. Syphilis can be effectively treated with antibiotics, specifically the preferred intramuscular penicillin G (given intravenously for neurosyphilis), or else ceftriaxone, and in those who have a severe penicillin allergy, oral doxycycline, or azithromycin.

Syphilis is believed to have infected 12 million people worldwide in 1999, with greater than 90% of cases in the developing world. After decreasing dramatically since the widespread availability of penicillin in the 1940s, rates of infection have increased since the turn of the millennium in many countries, often in combination with human immunodeficiency virus (HIV). This has been attributed partly to unsafe sexual practices among men who have sex with men, increased promiscuity, prostitution, and decreasing use of barrier protection.

As set forth above, diagnosis of syphilis is usually through blood tests. There are presently two types of serological tests used for the diagnosis and treatment of syphilis infection: treponemal tests, which utilize antigens prepared from the causative agent treponema pallidum, and non-treponemal tests, which employ antigens not derived directly from the causative agent.

The Centers for Disease Control (CDC), Atlanta, Ga., recommends that syphilis screening, and the assessment of treatment, be performed first using non-treponemal tests because it is believed that non-treponemal tests are more sensitive. In such tests, a false positive is possible. The CDC further recommends that positive screening test results be confirmed with a treponemal test. It is noted that the non-treponemal tests can be used for monitoring post-treatment and for detection of re-infection. There are currently two non-treponemal tests in common usage: the Venereal Disease Research Laboratory (VDRL) Test and the Rapid Plasma Reagin (RPR) Test.

The VDRL Test is a non-treponemal serological screening for syphilis used to assess response to therapy, to detect CNS involvement, and as an aid in the diagnosis of congenital syphilis. The basis of the test is that antibody (IgG, IgM or IgA), produced by a patient with syphilis, reacts with a compound comprised of cardiolipin, cholesterol, and lecithin. The test is performed by mixing the patients serum with compound described above. Positive sera result in "flocculation." Simply put, the VDRL Test is a manual coagulation test with a qualitative, subjective, visual readout requiring the use of a microscope. More specifically, a sample of the patient's antibody is mixed in a test tube, or on a microscope slide. A clinician is required to view the test tube, or slide and determine, based upon the clinician's own experience and training, if the visual presentation indicates coagulation to an extent sufficient to call the results positive. Quantitative test results require a serial dilution of the test sample and testing of multiple dilutions. Thus, the VDRL Test is labor intensive and unable to be automated. It is known that false negatives arise in the VDRL Test due to the Prozone Effect, or "Hook" Effect, in cases of strongly positive samples.

The RPR Test is a particle agglutination test. The RPR Test also is a manual test, with a qualitative, subjective, visual readout. The RPR Test utilizes a colloidal suspension of cardiolipin, cholesterol, and lecithin, mixed with micro-particulate carbon. Thus, the RPR Test uses the same antigen as the VDRL Test, but, in the RPR Test, the antigen has been bound to a carbon particle to allow visualization of the flocculation reaction without the need of a microscope. The mixture is placed on a test area of a card and the clinician is able to read the results based upon a visually detectable clumping of the carbon particles. Like the VDRL Test, the RPR Test is a quantitative test where the results require a serial dilution of the test sample and testing of multiple dilutions. Thus, the RPR Test is labor intensive and unable to be automated. Similarly, false negatives arise due to the Prozone Effect. FIG. 1 is a photograph of a RPR Test card. The clumping of the carbon particles is shown in a positive test result on the left (circle number 9). The right test area of the card (circle number 10), in contrast, where no clumping has occurred, is indicative of a negative result.

Three components comprise the VDRL antigen: cardiolipin; cholesterol; and lecithin. These components are lipid in nature. As such, they are not soluble in aqueous solution. In the classical VDRL test, therefore, the three-component antigen complex is used as a colloidal suspension. It must be prepared under very carefully controlled conditions, just prior to performing the test. Due to its inherent lack of stability, the colloidal suspension must be prepared daily for immediate use. Because of the inherent unstable property, there is no way to preserve the mixed antigens in colloidal suspension for long periods of time. It would be beneficial to provide a sensitive and specific non-treponemal syphilis screening and assessment of treatment test, that is stable and has a long shelf life.

Neither the VDRL Test nor the RPR Test lend themselves to automation. It would be beneficial to provide a syphilis screening and assessment of treatment test that is able to be automated.

A need exists to overcome the problems with the prior art systems, designs, and processes as discussed above.

SUMMARY OF THE INVENTION

The invention provides serological methods and diagnostic tests for syphilis antibodies that overcome the hereinaforementioned disadvantages of the heretofore-known devices and methods of this general type and enables automation and the test has a long shelf life.

The serological methods and diagnostic tests for syphilis antibodies according to the invention combine features of the non-treponemal VDRL Test with the Enzyme Linked Immunosorbent Assay (ELISA) process to create an inventive VDRL ELISA Test. ELISA is a test that uses antibodies and color change to identify a substance. It is a type of analytic biochemistry assay that uses a solid-phase enzyme immunoassay (EIA) to detect the presence of a substance, usually an antigen or an antibody, in a liquid sample or wet sample.

The steps of ELISA, in this iteration also referred to as "indirect" ELISA, follows the mechanism below:
- A buffered solution of the antigen is added to each well of a microtiter plate, where it is given time to adhere to the plastic through charge interactions.
- A solution of non-reacting protein, such as bovine serum albumin or casein, is added to block any plastic surface in the well that remains uncoated by the antigen.
- The primary antibody is added, which binds specifically to the test antigen coating the well. This primary antibody could also be in the serum of a donor to be tested for reactivity towards the antigen. After a suitable incubation period, the unbound antibody is decanted and the wells are rinsed with a buffered solution.
- A secondary antibody is added, which will bind the primary antibody. This secondary antibody has an enzyme attached to it, which has a negligible effect on the binding properties of the antibody. After a suitable incubation period, the unbound antibody is decanted and the wells are rinsed with a buffered solution.
- A substrate for this enzyme is then added. Often, this substrate changes color upon reaction with the enzyme. The color change shows the secondary antibody has bound to primary antibody, which strongly implies the donor has had an immune reaction to the test antigen. The higher the concentration of the primary antibody present in the serum, the stronger the color change. Often, a spectrometer is used to give quantitative values for color strength.

In ELISA, the enzyme acts as an amplifier; even if only few enzyme-linked antibodies remain bound, the enzyme molecules will produce many signal molecules. Within common-sense limitations, the enzyme can go on producing color indefinitely, but the more primary antibody is present in the donor serum, the more secondary antibody+enzyme will bind, and the faster the color will develop.

ELISA may be run in a qualitative or quantitative format. Qualitative results provide a simple positive or negative result (yes or no) for a sample. The cutoff between positive and negative is determined by the analyst and may be statistical. The addition of two or three times the standard deviation (error inherent in a test) of the mean value obtained for known negative samples, is often used to distinguish positive from negative samples. In quantitative ELISA, the optical density (OD) of the sample is compared to a standard curve, which is typically a serial dilution of a known-concentration solution of the target molecule. For example, if a test sample returns an OD of 1.0, the point on the standard curve that gave OD=1.0 must be of the same analyte concentration as the sample.

In sharp contrast to the VDRL and RPR Tests, the VDRL ELISA Test of the invention, is an enzyme immunoassay, the results of which can be read objectively with a spectrophotometer. The inventive syphilis test is, therefore, capable of producing standardized, quantitative, and reproducible results, in a single test and to do so in automation. The VDRL ELISA Test is as sensitive and specific as both the VDRL and RPR test and is compatible with a wide variety of automated analyzers.

The VDRL and RPR Tests are performed using the antigen complex in the form of a colloidal suspension. In contrast, the antigen complex used in the inventive VDRL ELISA Test is prepared by dissolving the three lipid components in a mixture of organic solvents. This produces a uniform, homogeneous antigen that can be accurately dispensed into microwells, and dried in place. This results in VDRL antigen wells that are uniformly coated. The uniformity of coating facilitates accurate and reproducible test results. The VDRL ELISA antigen coated wells may be stored for extended periods then used to perform an ELISA test. Heretofore, it has been generally understood that wells coated with the VDRL antigen complex could not be stored for extended periods of time and, after such storage, be used to perform in an ELISA test in an accurate and reproducible manner.

The exemplary embodiments described herein utilize microwells, for example, polystyrene microwells, as the solid-phase of the VDRL ELISA test. Use of the term microwells is not to be taken as limiting any platform of any embodiment only to such microwells. This term, as used anywhere herein, is defined as equally including all other solid-phase platforms that can be substituted for microwells, which platforms are defined to include, but are not limited to, microtubes, columns, beads, dipsticks, nitrocellulose membranes, lateral flow devices, and other containers, to name a few. As such, the solid-phase platforms can also be described in general as containers.

The design of the VDRL ELISA Test is significantly improved over the prior art and permits quantization and standardization of the test results, as follows:
1) A kit calibrator facilitates standardization and normalization of the test results. The calibrator(s) is a standard serum sample that is traceable to a primary, or secondary, standard, and has been assigned a known value. The calibrator(s) is included with the patient samples in each test run to produce a result of known value against which patients test results may be compared and thereby interpreted as either positive or negative.
2) The kit's negative and positive controls facilitate the validation of the test results. The positive and negative controls are serum samples that have been assigned expected value ranges and that are included with the patient samples in each test run. If the values obtained for the positive and negative controls fall within their assigned ranges when compared to the kit calibrator, the results obtained for the patient samples are valid, if the values do not fall within the assigned ranges, the results obtained for the patient samples are invalid and the test must be repeated.

The formulations contributing to the sensitivity and specificity of the VDRL ELISA Test include the following:

1) The formulation, i.e., relative concentrations of the cardiolipin, cholesterol, lecithin antigen preparation, contributes to the sensitivity and specificity of the test.
2) The formulation of a post-coating solution prevents non-specific binding of human antibody to the antigen-coated wells.
3) The formulation of a sample diluent prevents the non-specific binding of human antibody to the antigen-coated wells. The sample diluent is a buffered solution that contains an inert protein that does not interfere with the binding of the patient antibody that is specifically directed against the antigen coated on the wells. Concurrently, the inert protein prevents the binding of extraneous patient antibody that is not specifically directed against the antigen coated on the wells, thereby preventing potentially false positive results.
4) In cases of very high levels of non-treponemal antibody, the VDRL ELISA Test is not subject to the Prozone or Hook Effect, which can lead to false negative results in the VDRL and RPR Tests.

The properties of the VDRL antigen mixture that have heretofore prevented the development of a stable and reproducible VDRL ELISA test, are as follows:
1) Cardiolipin, a major component of the VDRL antigen preparation, is inherently unstable.
2) Cardiolipin and the other components of the antigen preparation, cholesterol and lecithin, are not soluble in aqueous solution and, therefore, cannot be bound to polystyrene wells by conventional measures.

The inventive systems and processes are not limited to particular cardiolipins or cholesterol. The inventive systems and processes are envisioned to use natural or purified-from-natural cardiolipins or even synthesized cardiolipins. It is possible that synthesized cardiolipins could be used even if they are inherently stable. The inventive systems and processes are envisioned to also be used with synthesized cholesterol and/or synthesized lecithin.

The following procedures were used to prepare VDRL antigen coated wells that are stable and capable of producing reproducible test results:
1) The cholesterol is initially dissolved in an organic solvent, and is then further diluted in an ethanol solution containing cardiolipin and lecithin.
2) A small volume (e.g., 50 microliter) of the antigen solution is permitted to evaporate in place, in polystyrene microwells.
3) The coated wells are rinsed once with buffered saline.
4) The antigen coating is then stabilized by overcoating with an inert protein dissolved in buffered saline.
5) The overcoat solution is decanted and the wells are air-dried and then sealed in vapor-proof pouches with desiccant.
6) The enzyme-labeled conjugate component of the test is formulated to be compatible with the lipid nature of the VDRL antigens coated on the wells.
7) The sample diluent is formulated to be compatible with the lipid nature of the VDRL antigens coated on the wells.
8) The wash fluid is formulated to be compatible with the lipid nature of the VDRL antigens coated on the wells.
9) The enzyme substrate is formulated to be compatible with the lipid nature of the VDRL antigens coated on the wells.

With the foregoing and other objects in view, there is provided, in accordance with the invention, a method of manufacturing a non-treponemal diagnostic test for syphilis infection, which comprises initially dissolving cholesterol in an organic solvent and further diluting the dissolved cholesterol in an ethanol solution comprising cardiolipin and lecithin to form an antigen solution, permitting a volume of the antigen solution to evaporate in place within a container and at least partially coat the container with an antigen coating, rinsing the at least partially coated container with buffered saline, stabilizing the antigen coating into a syphilis antigen complex by overcoating the antigen coating with an overcoat solution comprising an inert protein, and decanting the overcoat solution, drying the container, and sealing the container in a vapor-proof pouch.

With the objects of the invention in view, there is also provided a method of manufacturing a non-treponemal diagnostic test for syphilis infection, which comprises initially dissolving cholesterol in an organic solvent and further diluting the dissolved cholesterol in an ethanol solution comprising cardiolipin and lecithin to form an antigen solution, permitting a volume of the antigen solution to evaporate in place within a container and at least partially coat the container with an antigen coating, rinsing the at least partially coated container with buffered saline, stabilizing the antigen coating into a syphilis antigen complex by overcoating the antigen coating with an overcoat solution comprising an inert protein, decanting the overcoat solution, drying the container, and sealing the container in a vapor-proof pouch, providing an enzyme-labeled conjugate component of a syphilis infection test that is formulated to be compatible with a lipid nature of the cholesterol, the cardiolipin, and the lecithin, providing a sample diluent that is formulated to be compatible with the lipid nature of the cholesterol, the cardiolipin, and the lecithin, providing a wash fluid that is formulated to be compatible with the lipid nature of the cholesterol, the cardiolipin, and the lecithin, and providing an enzyme substrate that is formulated to be compatible with the lipid nature of the cholesterol, the cardiolipin, and the lecithin.

With the objects of the invention in view, there is also provided a non-treponemal diagnostic test for syphilis infection comprising a container having an interior that is at least partially coated first with a mixture of cholesterol dissolved in an organic solvent and further diluted in an ethanol solution comprising cardiolipin and lecithin to form an interior antigen coating that is then overcoated with an inert protein dissolved in buffered saline, a vapor-proof pouch sealing the container therein after the overcoating is dry, an enzyme-labeled conjugate component of a syphilis infection test formulated to be compatible with a lipid nature of the cholesterol, the cardiolipin, and the lecithin, a sample diluent formulated to be compatible with the lipid nature of the cholesterol, the cardiolipin, and the lecithin, a wash fluid formulated to be compatible with the lipid nature of the cholesterol, the cardiolipin, and the lecithin, and an enzyme substrate formulated to be compatible with the lipid nature of the cholesterol, the cardiolipin, and the lecithin.

In accordance with another mode of the invention, the volume of the antigen solution is approximately 50 microliters.

In accordance with a further mode of the invention, the container is one or more of a microwell, a polystyrene microwell, a microtube, a column, a bead, a dipstick, a nitrocellulose membrane, and a lateral flow device.

In accordance with an added mode of the invention, the organic solvent is one or more of acetone, chloroform, butanol, methanol, or ether.

In accordance with an additional mode of the invention, the cholesterol is a natural cholesterol, a purified-from-natural cholesterol, and/or a synthesized cholesterol.

In accordance with yet another mode of the invention, the cardiolipin is a natural cardiolipin, a purified-from-natural cardiolipin, and/or a synthesized cardiolipin.

In accordance with yet a further mode of the invention, the lecithin is a natural lecithin, a purified-from-natural lecithin, and/or a synthesized lecithin.

In accordance with yet an added mode of the invention, the container is air-dried.

In accordance with yet an additional mode of the invention, there is provided the step of sealing the container in the vapor-proof pouch with desiccant.

In accordance with again another mode of the invention, the overcoating step is carried out with the inert protein selected from one or more of bovine serum, bovine serum albumin, fetal bovine serum, gelatin, goat serum, horse serum, and milk protein.

In accordance with again a further mode of the invention, the overcoating step is carried out by dissolving the inert protein in buffered saline.

In accordance with again an added mode of the invention, the overcoating step is carried out by leaving the saline solution of the inert protein in the at least partially coated container for a period of time sufficient to allow the inert protein to bind to non-coated portions of the container.

In accordance with again an additional mode of the invention, the period of time is at least one of between approximately 30 minutes and approximately 5 hours, between approximately 1 and approximately 3 hours, between approximately 1.5 and approximately 2.5 hours, or approximately 2 hours.

In accordance with still another mode of the invention, the stabilized antigen coating overcoated with the inert protein has a shelf life of between approximately 6 months and approximately 1 year.

In accordance with still a further mode of the invention, the container is one or more of a microwell, a polystyrene microwell, a microtube, a column, a bead, a dipstick, a nitrocellulose membrane, and a lateral flow device.

In accordance with still an added mode of the invention, there is provided the steps of providing an enzyme-labeled conjugate component of a syphilis infection test that is formulated to be compatible with a lipid nature of the cholesterol, the cardiolipin, and the lecithin, providing a sample diluent that is formulated to be compatible with the lipid nature of the cholesterol, the cardiolipin, and the lecithin, providing a wash fluid that is formulated to be compatible with the lipid nature of the cholesterol, the cardiolipin, and the lecithin, and providing an enzyme substrate that is formulated to be compatible with the lipid nature of the cholesterol, the cardiolipin, and the lecithin.

In accordance with still an additional mode of the invention, there is provided the steps of adding serum of a donor to be tested for reactivity towards the syphilis antigen complex into the container and allowing the syphilis antibody to bind to the antigen coating if the syphilis antibody exists in the patient's serum, rinsing the container with buffered saline, adding a secondary antibody designed to bind to the primary antibody in the serum to the container, the secondary antibody having an attached enzyme that changes color when the enzyme substrate for the enzyme is added thereto and reacts with the enzyme, rinsing the container with buffered saline, and adding the enzyme substrate to produce a color change if the serum contains the syphilis antibody.

In accordance with another mode of the invention, there is provided the step of examining contents of the container with an automated spectrophotometric analyzer to detect the color change of the tested serum and, if there is a color change showing that the secondary antibody has bound to the primary antibody, forming a test result concluding that the donor of the serum has had an immune reaction to the test syphilis antigen.

In accordance with a concomitant mode of the invention, there is provided the step of producing with the spectrophotometer quantitative values corresponding to a strength of the color change.

Although the invention is illustrated and described herein as embodied in serological methods and diagnostic tests for syphilis antibodies, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which.

DETAILED DESCRIPTION OF THE INVENTION

Figure 1:
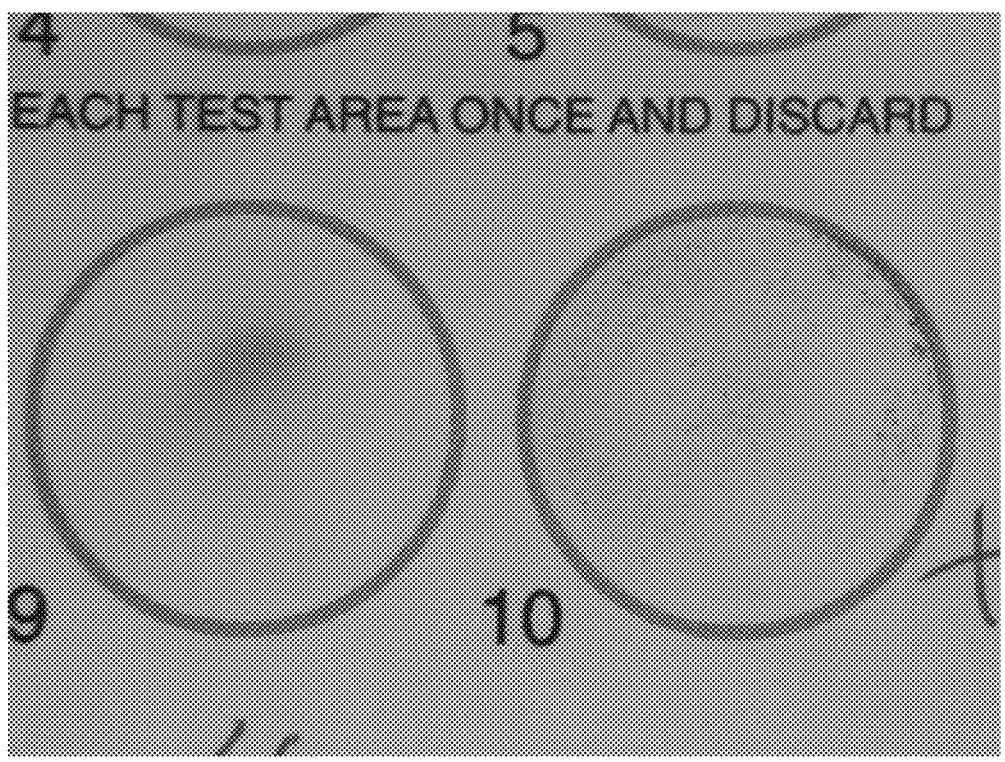
FIG. 1 is a photograph of a portion of an RPR Test card showing one test area with a positive result and one test area with a negative result.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

DEFINITIONS

Before the present invention is disclosed and described, it is to be understood that the terminology herein is not intended to be limiting and is only being used for the purpose of describing particular embodiments. Unless otherwise specified, all technological terms used herein have the same meaning as commonly understood by one of ordinary skill in the art to which the present invention belongs.

Alternate embodiments may be devised without departing from the spirit or the scope of the invention. Additionally, well-known elements of exemplary embodiments of the invention will not be described in detail or will be omitted so as not to obscure the relevant details of the invention.

As used herein, the terms "a" or "an", are defined as one or more than one. The term "plurality", as used herein, is defined as two or more than two. The term "another", as used herein, is defined as at least a second or more.

As used herein, the terms "including" and/or "having", are defined as comprising (i.e., open language). The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, relational terms, such as first and second, may be used solely to distinguish one entity or action from another entity or action without necessarily requiring or implying any actual such relationship or order between such entities or actions.

As used herein, the term "coupled" is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to the figures of the drawings in detail and first, particularly to FIG. 2, there is shown a first exemplary embodiment of a process for creating and manufacturing a VDRL ELISA Test. The inventive VDRL ELISA Test starts with the previous understanding that the antigen complex for syphilis is formed from a combination of cardiolipin, cholesterol and lecithin, which, due to its lipid nature, does not readily remain in a microwell. From this, it was necessary to find a way to obtain a deposition of the antigen complex in a microwell that not only remains for periods of time sufficient to perform a non-treponemal test for syphilis, but also to perform that test with microwells having a desirably long shelf life.

Figure 2:
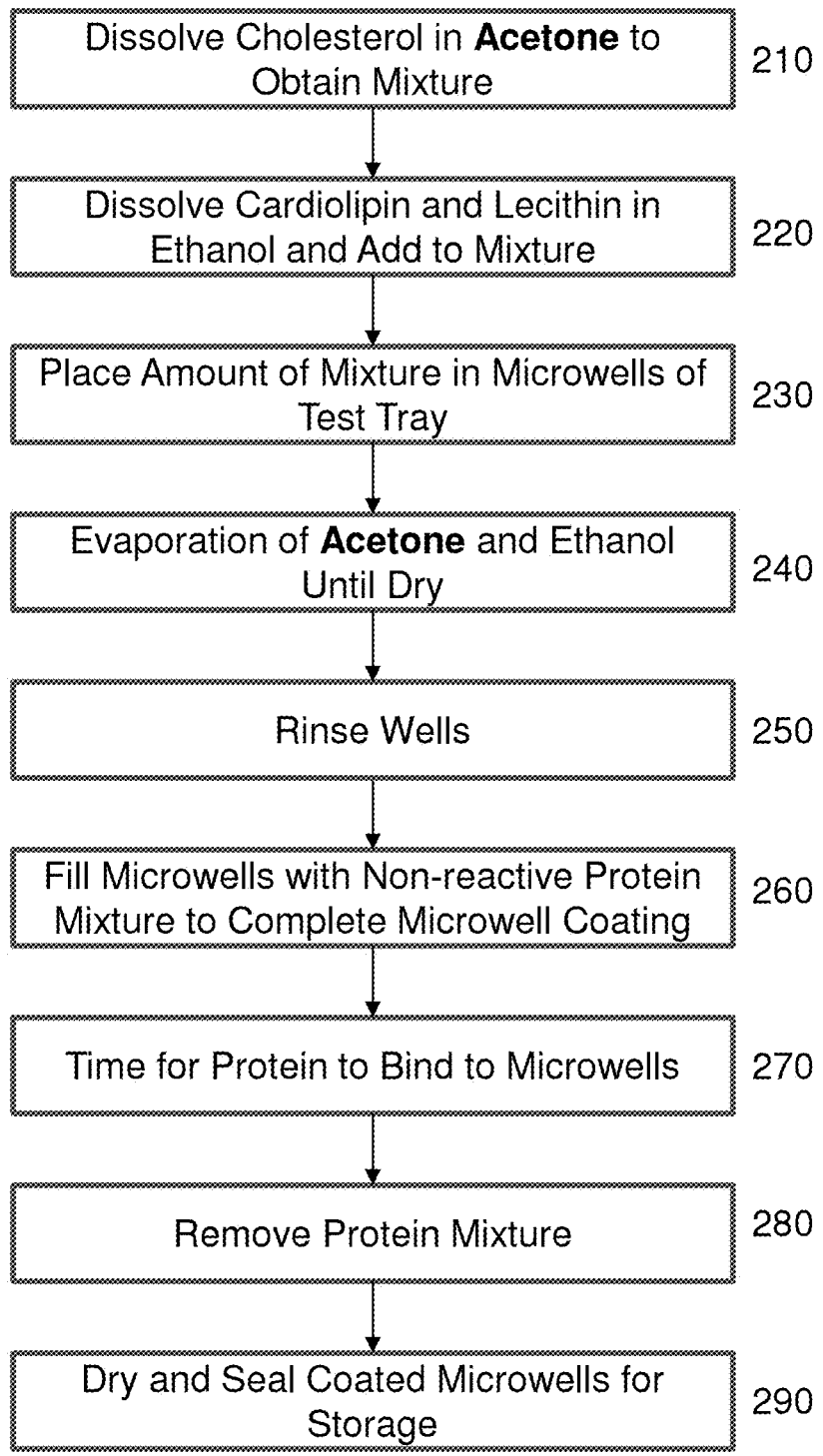
FIG. 2 is a process flow diagram for manufacturing an exemplary embodiment of a VDRL ELISA Test.

The process for creating such a microwell according to the invention is illustrated with the flow chart of FIG. 2. It is noted that, as described above, use of the term "microwells" in the exemplary embodiments is not to be taken as limiting the platform only to microwells and equally includes all other solid-phase platforms can be substituted for microwells, which can include microtubes, columns, beads, dipsticks, nitrocellulose membranes, and lateral flow devices.

As set forth above, the non-binding of the antigen complex to a microwell is due the lipid nature of cardiolipin, cholesterol and lecithin, which compounds are not soluble in aqueous solution. The inventors discovered, however, that these compounds can be dissolved in organic solvents and dried in wells without a deleterious affect upon the compounds. The inventors have further discovered that the relative proportions of the compounds used in the classical VDRL method, when diluted to one-tenth the concentration, i.e., 0.003% W/V cardiolipin, 0.09% W/V cholesterol and 0.02% W/V lecithin, produce the desired results when dried in wells in the VDRL-ELISA method. Furthermore, by examining the aforementioned compounds in the VDRL ELISA method, either separately or in various relative proportions, the inventors determined that the relative concentrations stated above are more reactive with non-treponemal syphilis antibodies than any of the compounds individually or in any of the other relative proportions examined. Accordingly, in Step 210, cholesterol is dissolved in an organic solvent, such as acetone, chloroform, butanol, methanol, and/or ether. In Step 220, cardiolipin and lecithin are dissolved in ethanol, and the organic solvent mixture is further diluted in the ethanol solution containing the cardiolipin and lecithin. In Step 230, the two mixtures are combined and an amount of this mixture is placed in microwells, for example, polystyrene microwells. In an exemplary embodiment, the amount of the mixture placed in each microwell is between approximately 40 and 60 microliters, in particular, approximately 50 microliters.

It is known that both the organic solvent and ethanol evaporate readily. From this, evaporation of the organic solvent and ethanol is allowed to occur in Step 240, which evaporation can be aided with air circulation devices such as fans. In an exemplary embodiment, the evaporation occurs at room temperature (20° C. to 25° C.). Evaporation continues until the liquid in the microwells has dried. At this point, the three components of the antigen complex become bound to the interior surface of the microwells. The microwells are washed once, for example, with buffered saline in Step 250.

After the microwells are coated with the antigen complex, it was found that this coating is not present on the entirety of the microwell interior. Where such uncoated portions occur, it is possible that, when used in the actual testing procedure, the test material (i.e., the patient's serum potentially containing the syphilis antibody) could bind or be adversely affected by the interior surface of the microwell. In such a case, the test material could bond to the non-coated surfaces and undesirably augment the result, which occurs, as set forth above, by spectrophotometric reading. In such a situation, the color reading will be more intense than it should be for that test specimen. Therefore, it would be desirable to prevent this detrimental situation from occurring. To solve this problem, the inventive manufacturing process binds a non-reactive compound to the uncoated portions of the microwells. The selected non-reactive compound is an inert protein, such as any one of bovine serum, bovine serum albumin, fetal bovine serum, gelatin, goat serum, horse serum, and milk protein, to name a few. Utilizing the known property that cardiolipin, cholesterol, and lecithin are not soluble in aqueous solution, in Step 260, the coated microwells are filled with a post-coating mixture of the inert protein dissolved in buffered saline. This aqueous solution is left in the microwells (not adversely affecting the coating of the antigen complex) in Step 270 for a given period of time sufficient to allow the inert protein to bind to the non-coated portions of the microwell. This post-coating soaking occurs for between approximately 30 minutes and approximately 5 hours, for example, between approximately 1 and approximately 3 hours, between approximately 1.5 and approximately 2.5 hours, and, in particular, for approximately 2 hours, resulting in a bond of the inert protein in all areas where the antigen complex does not appear. Removal of the inert protein soak occurs in Step 280 by decanting or aspirating the remaining solution. The microwell interiors are air dried and then sealed in vapor-proof pouches with desiccant in Step 290. When the so-coated microwells are packaged with desiccant, it was discovered that the antigen complex and the post-coating inert protein remained stable for many months, which stability was found to be augmented by the non-specific binding of the inert protein. In such a packed state, the shelf-life of the so-coated interior is at least 12 months. In particular, the shelf-life is between 6 months and 1 year.

Figure 3:
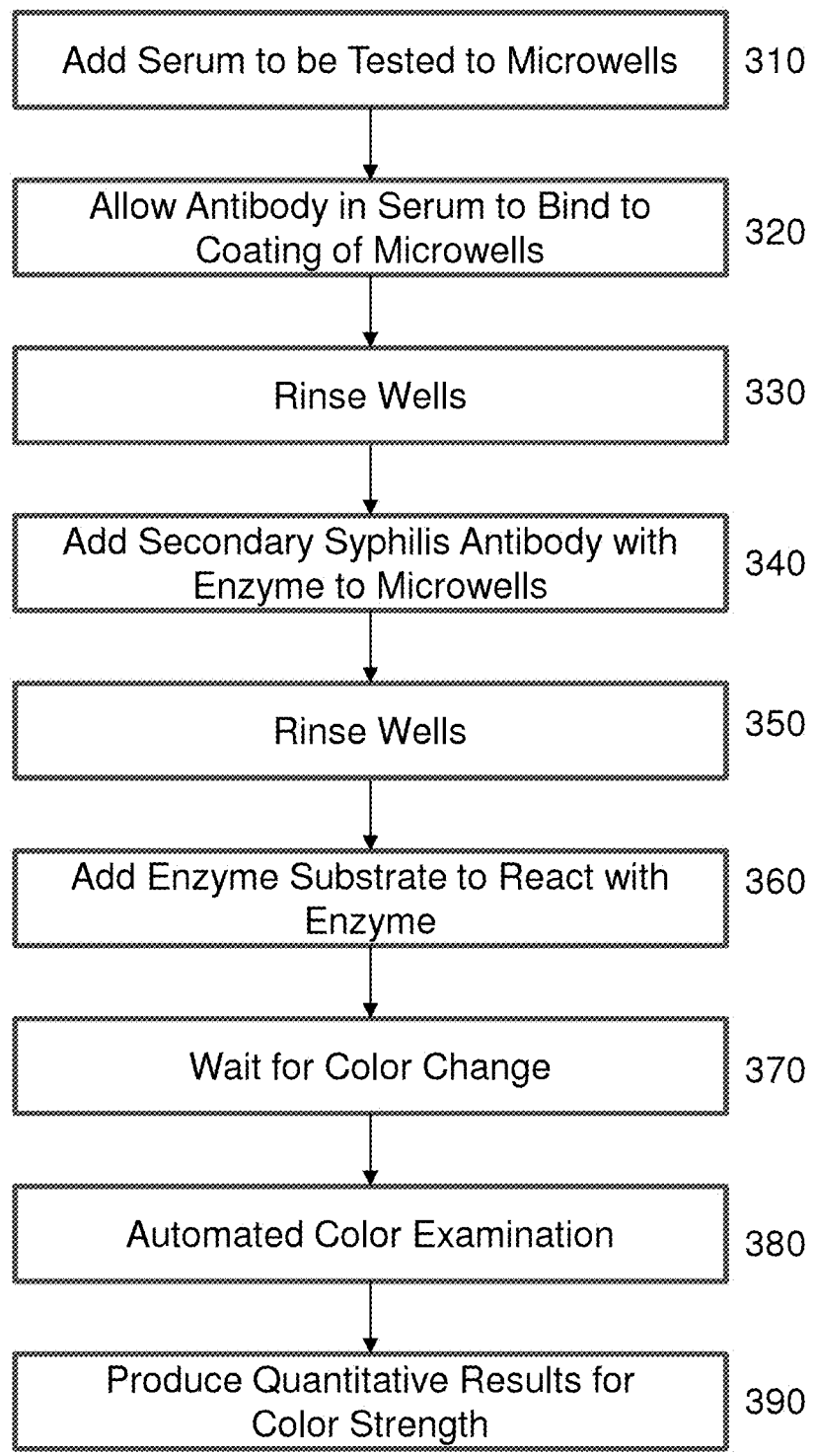
FIG. 3 is a process flow diagram for conducting the VDRL ELISA Test.
Figure 4:
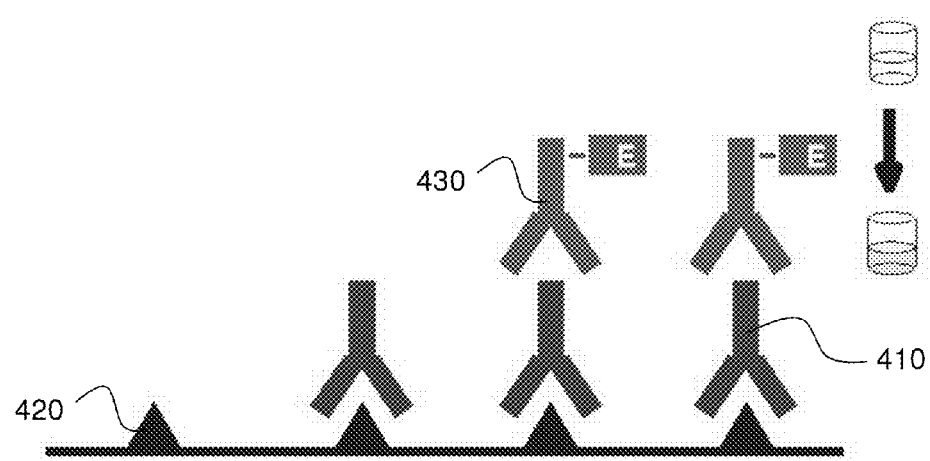
FIG. 4 is a diagram illustrating the reaction in the VDRL ELISA Test.
Figure 5:
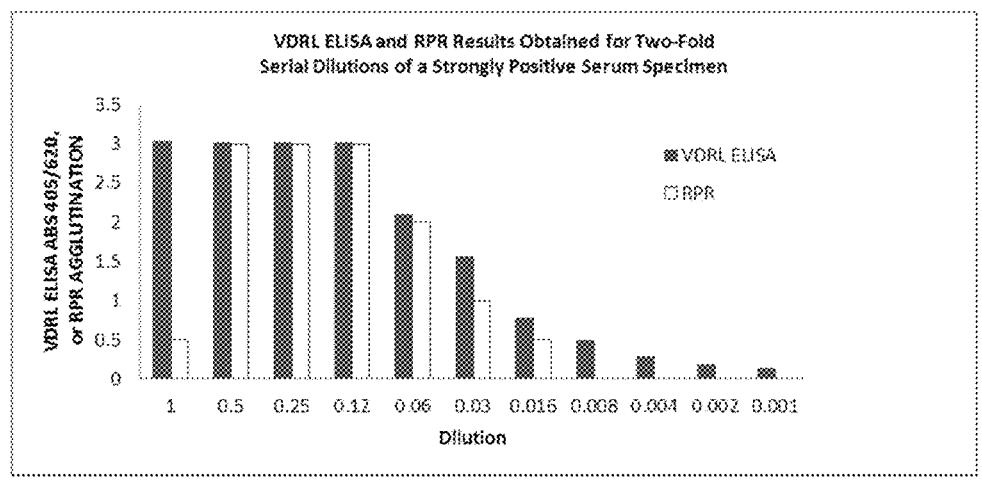
FIG. 5 is a graph illustrating a comparison of results between the VDRL ELISA Test and the RPR Test and demonstrating a prozone or "hook" effect in the RPR test.

With these coated microwells, the steps of the VDRL ELISA Test follow the mechanism below and is illustrated with reference to the flow chart of FIG. 3 and the diagram of FIG. 4. In Step 310, the serum 410 of a donor to be tested for reactivity towards the syphilis antigen complex 420 is added into one or more microwells in a microtiter plate. Because the syphilis antigen complex 420 coats each microwell, if the syphilis antibody exists in the patient's serum 410 binds, that antibody will bind to the coating 420 in Step 320. The microwell is rinsed, for example, with buffered saline in Step 330. A secondary antibody 430 is added in Step 340, which antibody 430 is designed to bind to the primary antibody in the serum 410, and the microwell is rinsed, for example, with buffered saline in Step 350. This secondary antibody 430 has an enzyme E attached to it, which has a negligible effect on the binding properties of the antibody. However, when a substrate for the enzyme E is added, the substrate will change color upon reaction with the enzyme E. This substrate is added in Step 360 to produce a color change in Step 370 if the serum 410 contains the syphilis antibody. An automated spectrophotometric analyzer examines the reactions in Step 380 to detect the color change of the tested serum 410. Any color change in the microwell shows that the secondary antibody 430 has bound to primary antibody 410, which strongly implies that the donor of the serum 410 has had an immune reaction to the test syphilis antigen. The higher the concentration of the primary syphilis antibody present in the serum 410, the stronger the color change will be in Step 370. The spectrophotometer produces, in Step 390, quantitative values for the color strength. As those having skill in the art know, this test entirely eliminates the Prozone Effect, which means, in practice, that a lab does not need to perform further testing where the sample is diluted and the sample is re-tested, perhaps repeatedly. The difference between the results of the VDRL ELISA Test and the tests that have the Prozone Effect is shown in the graph of FIG. 5, where a plateau occurs in the inventive test with later titration demonstrating a decreasing the dose effect. Moreover, this test is able to be readily and easily automated by standard automated spectrophotometric analyzers. It has been found that the sensitivity is at least as equivalent to the RPR and VDRL Tests but the long shelf life and ability to be automated (thereby eliminating the need for subjective analysis by a clinician).

The classical non-treponemal tests, VDRL and RPR, are known to detect both IgG and IgM class antibodies, but they not capable of distinguishing between the two antibody classes. The inventors are aware that the VDRL ELISA Test can be modified based upon the specificity of the enzyme-labeled conjugate being used in the test. Therefore, it is possible to detect IgG only, IgM only, or both. In one iteration, the VDRL test can be used for screening for the presence of non-treponemal syphilis antibodies in adults by employing conjugates that detect both IgG and IgM. This is the approach recommended by the Centers for Disease Control (CDC) for syphilis screening. In another iteration, the VDRL ELISA Test can be modified to detect only IgM antibodies. It is known that IgM antibodies of maternal origin do not cross the placental barrier, therefore, IgM antibodies to syphilis detected in the newborn's serum is an indication of syphilis infection in the newborn. It follows that this iteration of the VDRL ELISA Test can be applied to the diagnosis of syphilis in the newborn in a novel exemplary embodiment of the VDRL ELISA Test.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of manufacturing a non-treponemal diagnostic test for syphilis infection, which comprises:
   initially dissolving cholesterol in an organic solvent and further diluting the dissolved cholesterol in an ethanol solution comprising cardiolipin and lecithin to form an antigen solution;
   permitting a volume of the antigen solution to evaporate in place within a container and at least partially coat the container with an antigen coating;
   rinsing the at least partially coated container with buffered saline;

stabilizing the antigen coating into a syphilis antigen complex by overcoating the antigen coating with an overcoat solution comprising an inert protein; and decanting the overcoat solution, drying the container, and sealing the container in a vapor-proof pouch.

2. The method according to claim 1, wherein the volume of the antigen solution is approximately 50 microliters.

3. The method according to claim 1, wherein the container is one or more of a microwell, a polystyrene microwell, a microtube, a column, a bead, a dipstick, a nitrocellulose membrane, and a lateral flow device.

4. The method according to claim 1, wherein the organic solvent is one or more of acetone, chloroform, butanol, methanol, or ether.

5. The method according to claim 1, wherein the cholesterol is a natural cholesterol, a purified-from-natural cholesterol, and/or a synthesized cholesterol.

6. The method according to claim 1, wherein the cardiolipin is a natural cardiolipin, a purified-from-natural cardiolipin, and/or a synthesized cardiolipin.

7. The method according to claim 1, wherein the lecithin is a natural lecithin, a purified-from-natural lecithin, and/or a synthesized lecithin.

8. The method according to claim 1, wherein the container is air-dried.

9. The method according to claim 1, which further comprises sealing the container in the vapor-proof pouch with desiccant.

10. The method according to claim 1, which further comprises carrying out the overcoating step with the inert protein selected from one or more of bovine serum, bovine serum albumin, fetal bovine serum, gelatin, goat serum, horse serum, and milk protein.

11. The method according to claim 1, which further comprises carrying out the overcoating step by dissolving the inert protein in buffered saline.

12. The method according to claim 11, which further comprises carrying out the overcoating step by leaving the saline solution of the inert protein in the at least partially coated container for a period of time sufficient to allow the inert protein to bind to non-coated portions of the container.

13. The method according to claim 12, wherein the period of time is at least one of:

between approximately 30 minutes and approximately 5 hours;

between approximately 1 and approximately 3 hours;

between approximately 1.5 and approximately 2.5 hours; or approximately 2 hours.

14. The method according to claim 1, wherein the stabilized antigen coating overcoated with the inert protein has a shelf life of between approximately 6 months and approximately 1 year.

15. The method according to claim 1, wherein the container is one or more of a microwell, a polystyrene microwell, a microtube, a column, a bead, a dipstick, a nitrocellulose membrane, and a lateral flow device.

16. The method according to claim 1, which further comprises:

providing an enzyme-labeled conjugate component of a syphilis infection test that is formulated to be compatible with a lipid nature of the cholesterol, the cardiolipin, and the lecithin;

providing a sample diluent that is formulated to be compatible with the lipid nature of the cholesterol, the cardiolipin, and the lecithin;

providing a wash fluid that is formulated to be compatible with the lipid nature of the cholesterol, the cardiolipin, and the lecithin; and providing an enzyme substrate that is formulated to be compatible with the lipid nature of the cholesterol, the cardiolipin, and the lecithin.

17. The method according to claim 16, which further comprises:

adding serum of a donor to be tested for reactivity towards the syphilis antigen complex into the container and allowing the syphilis antibody to bind to the antigen coating if the syphilis antibody exists in the patient's serum;

rinsing the container with buffered saline;

adding a secondary antibody designed to bind to the primary antibody in the serum to the container, the secondary antibody having an attached enzyme that changes color when the enzyme substrate for the enzyme is added thereto and reacts with the enzyme;

rinsing the container with buffered saline; and adding the enzyme substrate to produce a color change if the serum contains the syphilis antibody.

18. The method according to claim 17, which further comprises examining contents of the container with an automated spectrophotometric analyzer to detect the color change of the tested serum and, if there is a color change showing that the secondary antibody has bound to the primary antibody, forming a test result concluding that the donor of the serum has had an immune reaction to the test syphilis antigen.

19. The method according to claim 18, which further comprises producing with the spectrophotometer quantitative values corresponding to a strength of the color change.

20. A method of manufacturing a non-treponemal diagnostic test for syphilis infection, which comprises:

initially dissolving cholesterol in an organic solvent and further diluting the dissolved cholesterol in an ethanol solution comprising cardiolipin and lecithin to form an antigen solution;

permitting a volume of the antigen solution to evaporate in place within a container and at least partially coat the container with an antigen coating;

rinsing the at least partially coated container with buffered saline;

stabilizing the antigen coating into a syphilis antigen complex by overcoating the antigen coating with an overcoat solution comprising an inert protein;

decanting the overcoat solution, drying the container, and sealing the container in a vapor-proof pouch;

providing an enzyme-labeled conjugate component of a syphilis infection test that is formulated to be compatible with a lipid nature of the cholesterol, the cardiolipin, and the lecithin;

providing a sample diluent that is formulated to be compatible with the lipid nature of the cholesterol, the cardiolipin, and the lecithin;

providing a wash fluid that is formulated to be compatible with the lipid nature of the cholesterol, the cardiolipin, and the lecithin; and providing an enzyme substrate that is formulated to be compatible with the lipid nature of the cholesterol, the cardiolipin, and the lecithin.

21. A non-treponemal diagnostic test for syphilis infection, comprising:

a container having an interior that is at least partially coated first with a mixture of cholesterol dissolved in an organic solvent and further diluted in an ethanol solution comprising cardiolipin and lecithin to form an interior antigen coating that is then overcoated with an inert protein dissolved in buffered saline;

a vapor-proof pouch sealing the container therein after the overcoating is dry;

an enzyme-labeled conjugate component of a syphilis infection test formulated to be compatible with a lipid nature of the cholesterol, the cardiolipin, and the lecithin;

a sample diluent formulated to be compatible with the lipid nature of the cholesterol, the cardiolipin, and the lecithin;

a wash fluid formulated to be compatible with the lipid nature of the cholesterol, the cardiolipin, and the lecithin; and an enzyme substrate formulated to be compatible with the lipid nature of the cholesterol, the cardiolipin, and the lecithin.

* * * * *